United States Patent
Lemay et al.

(10) Patent No.: US 7,727,208 B2
(45) Date of Patent: Jun. 1, 2010

(54) ERGONOMIC TAMPON APPLICATOR

(75) Inventors: Jessica E. Lemay, Paramus, NJ (US);
Kathryn G. Bennett, Fairfield, CT (US);
Keith J. Edgett, Ramsey, NJ (US); **Dane
R. Jackson**, Bloomingdale, NJ (US);
Mario A. Turchi, Tenafly, NJ (US);
Susanne Weber, New York, NY (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 10/242,474

(22) Filed: Sep. 12, 2002

(65) Prior Publication Data
US 2004/0054317 A1    Mar. 18, 2004

(51) Int. Cl.
*A61F 13/20* (2006.01)
*A61F 13/15* (2006.01)

(52) U.S. Cl. ............ 604/385.17; 604/385.18; 604/904; 604/11; 604/12; 604/13; 604/14; 604/385.01

(58) Field of Classification Search ............ 604/904, 604/385.17, 385.18, 285, 286, 11–18, 311, 604/385.01
See application file for complete search history.

(56) References Cited

U.S. PATENT DOCUMENTS

| | | | |
|---|---|---|---|
| 652,848 A | 7/1900 | Hill | |
| 1,191,736 A | 7/1916 | Roberson | |
| 2,476,956 A | 7/1949 | Bonham | 604/15 |
| 2,489,502 A | 11/1949 | Ruth | 604/18 |
| 2,587,717 A | 3/1952 | Fourness | 604/18 |
| D197,751 S | 3/1964 | Rigney et al. | D83/12 |
| 3,139,886 A | 7/1964 | Tallman et al. | 604/12 |
| 3,575,169 A | 4/1971 | Voss et al. | 604/18 |
| 3,628,533 A * | 12/1971 | Loyer | 604/14 |
| 3,765,416 A | 10/1973 | Werner et al. | 128/263 |
| 4,048,998 A | 9/1977 | Nigro | 604/14 |
| 250,663 A | 12/1978 | Koch et al. | D24/99 |

(Continued)

FOREIGN PATENT DOCUMENTS

EP    0418791 A1    9/1990

(Continued)

OTHER PUBLICATIONS

International Search Report, dated May 11, 2004.

(Continued)

*Primary Examiner*—Jacqueline F. Stephens
(74) *Attorney, Agent, or Firm*—Ohlandt, Greeley, Ruggiero & Perle, L.L.P

(57) ABSTRACT

The present invention is directed to an ergonomically improved tampon applicator having a plunger and a barrel. The barrel has four distinct sections, namely a finger grip section, a reverse taper section, a main body section, and an insertion tip section. The reverse taper section is tapered towards the fingergrip section and the main body section is tapered in an opposite direction towards the insertion tip section. A maximum diameter is formed where the reverse taper section and main body section meet on the barrel. The maximum diameter provides a sensory means to the user to alert the user when the applicator has been inserted at the proper depth in the vagina.

37 Claims, 2 Drawing Sheets

U.S. PATENT DOCUMENTS

| | | | | |
|---|---|---|---|---|
| 4,198,978 A | | 4/1980 | Nigro | 128/285 |
| 4,361,150 A | | 11/1982 | Voss | 604/15 |
| 4,421,504 A | | 12/1983 | Kline | 604/12 |
| 4,428,370 A | * | 1/1984 | Keely | 128/838 |
| 4,508,531 A | * | 4/1985 | Whitehead | 604/14 |
| 4,536,178 A | * | 8/1985 | Lichstein et al. | 604/15 |
| 4,676,773 A | * | 6/1987 | Sheldon | 604/16 |
| 4,846,802 A | | 7/1989 | Sanders, III | 604/15 |
| 4,891,042 A | | 1/1990 | Melvin et al. | 604/18 |
| 4,921,474 A | * | 5/1990 | Suzuki et al. | 604/16 |
| 5,080,659 A | | 1/1992 | Nakanishi | 604/904 |
| 5,158,535 A | | 10/1992 | Paul et al. | 604/15 |
| 5,290,501 A | | 3/1994 | Klesius | 264/322 |
| 5,788,663 A | | 8/1998 | Igaue et al. | 604/15 |
| D415,565 S | | 10/1999 | Hayes et al. | D24/141 |
| 6,045,526 A | | 4/2000 | Jackson | 604/15 |
| 6,264,626 B1 | | 7/2001 | Linares et al. | 604/15 |
| 6,364,854 B1 | | 4/2002 | Ferrer et al. | 604/60 |
| 6,368,442 B1 | | 4/2002 | Linares et al. | 156/198 |
| 6,423,025 B1 | | 7/2002 | Buzot | 604/15 |
| 6,432,075 B1 | | 8/2002 | Wada et al. | 604/15 |
| 6,432,076 B1 | | 8/2002 | Wada et al. | 604/15 |
| 6,478,764 B1 | | 11/2002 | Suga | 604/15 |
| 7,172,573 B1 | * | 2/2007 | Lamb | 604/59 |

FOREIGN PATENT DOCUMENTS

| | | |
|---|---|---|
| JP | 04322647 A | 11/1992 |
| JP | 04322648 A | 11/1992 |

OTHER PUBLICATIONS

U.S. Appl. No. 10/619,892, filed Jul. 15, 2003, LeMay et al.
U.S. Appl. No. 10/619/677, filed Jul. 15, 2003, LeMay et al.

* cited by examiner

ERGONOMIC TAMPON APPLICATOR

BACKGROUND OF THE INVENTION

1. Field of the Invention

The present invention relates generally to an improved tampon or tampon applicator. More particularly, the present invention relates to a tampon applicator with a barrel that has a reverse taper section for improved ease of use and user comfort.

2. Description of the Prior Art

Commercial tampon applicators typically consist of a barrel and a plunger used to expel an absorbent pledget housed in the barrel. The barrel is typically sub-divided into three sections, namely a finger grip, an insertion tip, and a main body section, which is located between the finger grip and insertion tip sections.

The finger grip section is typically the same diameter as the main body section of the barrel, but some designs (e.g., Playtex® Gentle Glide®) have a reduced diameter grip for improve grippability. The main body section is typically linear, except on plastic molded barrels where there is a slight taper to improve release characteristics from the manufacturing mold. The insertion tip section on some types of barrels have "petals" which curve over and enclose the pledget (i.e., rounded tip) housed in the barrel, but readily flex outwardly as the pledget is expelled through the insertion tip.

SUMMARY OF THE INVENTION

It is an object of the present invention to provide a tampon applicator that is ergonomic.

It is another object of the present invention to provide such an ergonomic tampon applicator with a plunger and a barrel.

It is still another object of the present invention to provide such an ergonomic tampon applicator barrel having a finger grip section, a reverse taper section, a main body section and an insertion tip section.

It is yet another object of the present invention to provide such an ergonomic tampon applicator barrel reverse taper section where the reverse taper is towards the finger grip section.

It is a further object of the present invention to provide such an ergonomic tampon applicator barrel finger grip section having a finger accepting region.

It is still a further object of the present invention to provide such an ergonomic tampon applicator insertion tip section formed with a plurality of petals.

It is yet a further object of the present invention to provide such an ergonomic tampon applicator main body section with a maximum diameter section that is sensually perceivable to a user to alert the user to the proper insertion depth of the applicator.

It is another object of the present invention to provide such an ergonomic tampon applicator having a plunger with at least one flared end.

These and other objects and advantages of the present invention will be appreciated from an ergonomically improved tampon applicator having a plunger and a barrel, of the present invention. The barrel has four distinct sections, namely a finger grip section, a reverse taper section, a main body section, and an insertion tip section. The reverse taper section is tapered towards the fingergrip section, and the main body section is tapered in an opposite direction towards the insertion tip section. A maximum diameter is formed where the reverse taper section and main body section meet on the barrel. The maximum diameter provides a sensory indicator to the user to alert the user when the applicator has been inserted to the proper depth in the vagina.

DETAILED DESCRIPTION OF THE INVENTION

Figure 1:
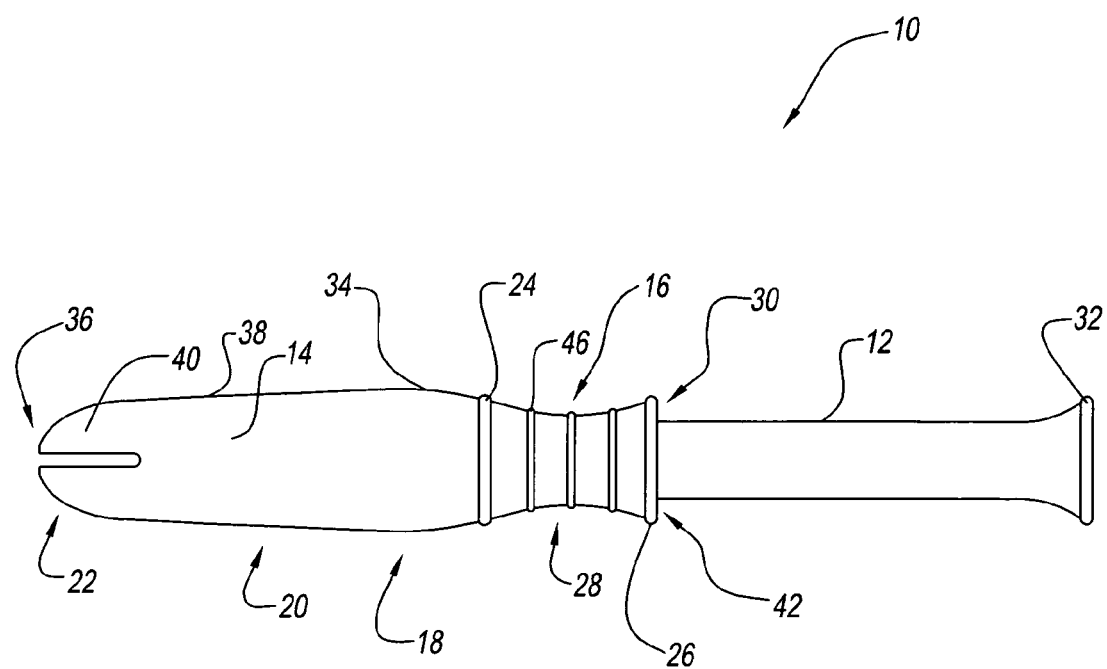
FIG. 1 is a plan view of a tampon applicator of the present invention.

Referring to drawings and, in particular, FIG. 1, there is shown an ergonomically improved tampon applicator according to the present invention generally represented by reference numeral 10. The ergonomically improved applicator 10 is easier to use and more comfortable to insert and remove. Applicator 10 includes a plunger 12 and a barrel 14.

Barrel 14 may be divided into four sections, as opposed to three sections typically found in prior art tampon applicators. The four sections include a finger grip section 16, a reverse taper section 18, a main body section 20, and an insertion tip section 22.

Finger grip section 16 is bound by a forward edge ridge 24 and a rearward edge ridge 26. Forward edge ridge 24 provides a firm grip surface during insertion of applicator 10 into the vaginal vault. Rearward edge ridge 26 provides a firm grip surface during expulsion of the pledget (not shown) and during removal of applicator 10 from the body. Forward and rearward edge ridges 24, 26 are about 6 mm to about 22 mm in diameter. Preferably, the forward and rearward edges 24, 26 are about 11 mm to about 17 mm in diameter, with about 14 mm being the most preferred diameter.

A finger accepting region 28 is formed between forward edge ridge 24 and rearward edge ridge 26. To ensure an adequate area to accept a user's finger or fingers, forward edge ridge 24 and rearward edge ridge 26 are spaced about 13 mm to about 40 mm apart. More preferably, forward edge ridge 24 and rearward edge ridge 26 are spaced about 17 mm to about 21 mm apart, with about 19 mm being the most preferred spacing. Finger accepting region 28 may be concave, convex, flat, or any combinations thereof. Preferably, region 28 is concave, which conforms to the contour of a user's finger. The maximum diameter of region 28 is preferably slightly less than the diameter of edge ridges 24, 26. Preferably, region 28 has a maximum to minimum diameter ratio of about 1.10 to about 1.75, with a more preferred ratio of about 1.25 to about 1.35.

Finger accepting region 28 may also include one or more gripping structures 46 to improve grippability of applicator 10. Suitable gripping structures 46 include, for example, one or more and preferably two or more, embossments, protuberances, slits, grooves, louvers, perforations, lances, abrasive medias, high wet coefficient of friction materials, pressure sensitive adhesives, or any combinations thereof. In addition, gripping structures 46 may be formed in any shape, including, for example, arc, circle, concave, cone, convex, diamond, line, oval, polygon, rectangle, rib, square, triangle, or any combinations thereof.

The maximum diameter 34 of applicator barrel 14 occurs at the forward end of reverse taper section 18. Reverse taper is meant to include a taper in the reverse direction, i.e. in a direction away from the insertion end of applicator 10, but not necessarily the same dimensional taper as main body section 20. The diameter of reverse taper section 18 tapers down toward forward edge ridge 24, where the diameter is equal to or slightly less than the diameter of forward edge ridge 24. This taper may be linear or curvilinear.

Maximum diameter 34 of barrel 14 exerts a slightly greater pressure than the smaller diameter portions of the barrel on the vaginal opening. This unique feature of barrel 14 provides a sensually perceivable way of signaling or indicating to a user that applicator 10 has been inserted to the correct depth in the vagina. Thus, the location of maximum diameter 34 along the length of barrel 14 is a critical aspect of the present invention. The location of maximum diameter 34 on barrel 14 is about 32 mm to about 54 mm in the axial direction of barrel 14 from forward end 36 of insertion tip 22. Preferably maximum diameter 34 is located about 40 mm to about 50 mm, and more preferably about 44 mm in the axial direction of barrel 14 from forward end 36 of insertion tip 22.

Main body section 20 is joined to reverse taper section 18 where maximum diameter 34 of barrel 14 is located. Main body section 20 tapers toward insertion tip section 22 in either a linear or curvilinear fashion so that its smallest diameter occurs where main body section 20 meets insertion tip section 22. The ratio of maximum diameter 34 to the diameter at the forward end 38 of main body section 20 is about 1.1 to about 1.5, and more preferably about 1.2 to about 1.3. This tapering of main body section 20 facilitates insertion comfort by gradually parting the vulva-vaginal channel over a longer length than that of only insertion tip section 22.

Insertion tip section 22 begins where there is a substantial change in the curvature of the forward portion of the barrel that is where the pledget-enclosing petals 40 are formed. In applicator designs where no petals are used, insertion tip 22 is the forward edge of the main body section 20 of barrel 14. The preferred insertion tip 22 is the petal type with a curvature that approximates an elliptical or hyperbolic curve. Preferably, insertion tip 22 has about 2 to about 12 petals, and more preferably about 3 to about 8 petals. The ratio of the maximum diameter of insertion tip section 22, which occurs at the plane where its rearward edge meets forward end 38 of main body section 20, to the total axial length of the insertion tip section along a horizontal axis of applicator 10, is about 0.9 to about 1.8, and more preferably about 1.1 to about 1.3.

The less severe curvature of insertion tip section 22 also facilitates insertion comfort by gradually parting the vulva-vaginal channel along its longer length.

It should be understood that while tampon applicator barrel 14 of the present invention is depicted as having four sections, namely a finger grip section, a reverse taper section, a main body section, and an insertion tip section, the tampon applicator barrel can include a reverse taper section and at least one additional section selected from a finger grip section, a main body section, an insertion tip section, or any combinations thereof.

The interior wall of barrel 14 that houses the pledget may have the same basic sidewall shape as its exterior wall. However, molding such a complicated interior wall requires a complex manufacturing process. Alternately, the interior wall can be practically straight walled (a slight taper may be required for tooling release) while the exterior wall has the sectional shapes discussed before, thus simplifying the molding process.

Figure 2:
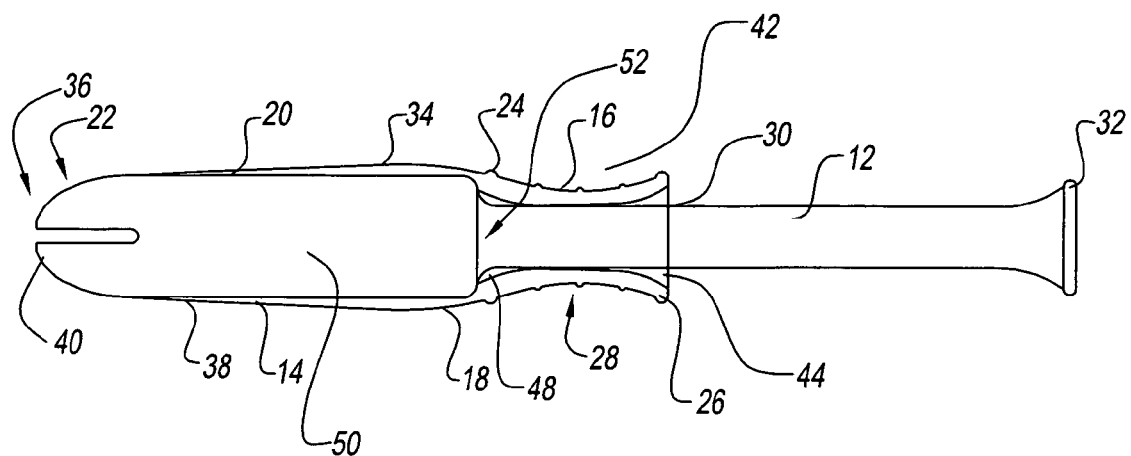
FIG. 2 is a cut away view of the tampon applicator of FIG. 1 depicting an absorbent pledget housed in the barrel.
Figure 3:
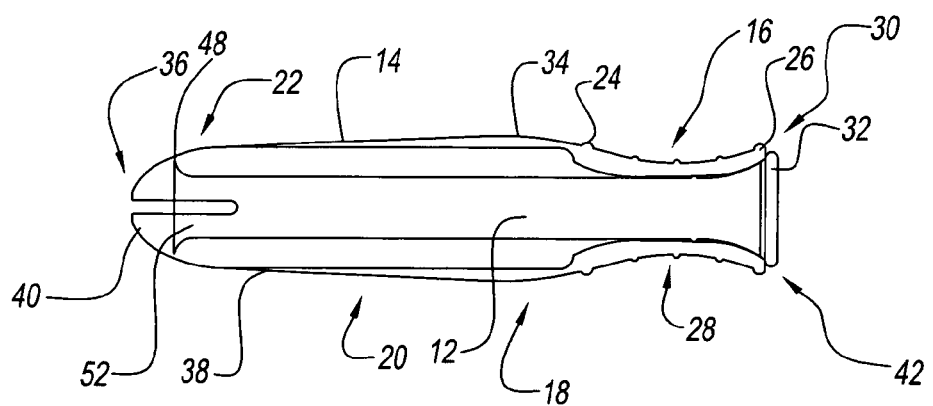
FIG. 3 is a cut away view of the tampon applicator of FIG. 2 after the pledget has been expelled from the barrel.

Referring to FIGS. 2 and 3, barrel 14 has a finger grip end 42. Plunger 12 telescopically fits into the finger grip end 42 of barrel 14. Plunger 12 has a diameter slightly smaller than the smallest diameter of finger receiving region 28 so that plunger 12 telescopically fits throughout the interior of barrel 14. Preferably, in one embodiment of the present invention, plunger 12 has a diameter about 4 mm to about 18 mm. More preferably, plunger 12 has a diameter about 5 mm to about 9 mm with the most preferred diameter being about 7 mm.

Plunger 12 has a first flare 32 at its distal end and a second flare or retaining structure 48 at its opposite barrel end 52. Finger grip section 16 has a plunger receiving end 30. Plunger receiving end 30 of finger grip section 16 has a chamfer 44 to receive first flare 32 of plunger 12 during pledget expulsion. This permits shortening the length of the section of plunger 12 that protrudes from barrel 14 since all of the protruded length is available for the telescopic action. This in turns results in a more ergonomic applicator. Such an ergonomic applicator is conducive to one handed use, since the distance between finger grip section 16 and first flare 32, where the fingertip is placed, is reduced by an amount equal to the length of first flare 32. Second flare or retaining feature 48 on barrel end 52 of plunger 12 prevents separation from barrel 14.

First flare 32 has a maximum diameter about 6 mm to about 22 mm. Preferably the maximum diameter is about 12 mm to about 16 mm, with about 13 mm being the most preferred maximum diameter, in order to provide a secure area for a user's fingertip during pledget expulsion. The rearward end of first flare 32 may be flat, concave, or convex. Preferably, it is concave to provide a secure area for the fingertip.

Second flare 48 has a maximum diameter about 5 mm to about 20 mm. Preferably the maximum diameter is about 11 mm to about 14 mm, with about 13 mm being the most preferred maximum diameter, in order to prevent separation from barrel 14.

Although it might be implied that the cross-sectional shape of plunger 12 and barrel 14 is circular, due to the use of the term 'diameter', it should be understood that the cross-sectional shape can be non-circular, such as oval or polygonal. Furthermore, the cross-sectional shape can vary along the length of both plunger 12 and barrel 14. For example, a circular plunger with a polygonal finger grip and an oval main body may be formed.

The pledget housed by applicator barrel 14 preferably has a tapered forward end that corresponds to that of insertion tip 22. The matching taper supports petals 40 during insertion of applicator 10 so that the petals cannot flex out of shape, thus enhancing comfort. Additionally, during expulsion from applicator 10, the pledget's tapered tip will gradually part the vaginal channel, further enhancing user comfort.

Suitable materials for forming plunger 12 and/or barrel 14 include, for example, biopolymer, cardboard, heat shrink plastic, paper slurry, plastic, plastic tubing, pulp slurry, pulp-molded paper, or any combinations thereof.

To reduce friction and/or increase strength, plunger 12 and/or barrel 14 may be coated with a coating material. Suitable coating materials include, for example, cellophane, cellulose, epoxy, lacquer, nitrocellulose, nylon, plastic, polyester, polylactide, polyolefin, polyvinyl alcohol, polyvinyl chloride, silicone, wax, or any combinations thereof.

The foregoing specification and drawings are merely illustrative of the present invention and are not intended to limit the invention to the disclosed embodiments. Variations and changes, which are obvious to one skilled in the art, are intended to be within the scope and nature of the present invention, which is defined in the appended claims.

What is claimed is:

1. A tampon applicator comprising:
   a plunger having a first end and a second end; and
   a barrel having a center axis, said barrel having an insertion tip section, a main body section adjacent said insertion tip section, a reverse taper section adjacent said main body section opposite said insertion tip section, and a finger grip section adjacent said reverse taper section opposite said main body section each entirely positioned about said center axis, said insertion tip section having a plurality of petals, wherein said insertion tip section begins where there is a substantial change in curvature of a forward portion of said barrel and terminates where said plurality of petals converge at said main body section, wherein said main body section is tapered toward said insertion tip section, wherein said reverse taper section is tapered toward said finger grip section in a direction away from said insertion tip section, and wherein said portions of said center axis in said insertion tip section, said main body section, said reverse taper section and said finger grip section are entirely in the same plane.

2. The tampon applicator of claim 1, wherein said taper of said main body section is selected from the group consisting of linear, curvilinear, and any combination thereof.

3. The tampon applicator of claim 1, wherein said finger grip section comprises a forward edge ridge and a rearward edge ridge opposite said forward edge ridge.

4. The tampon applicator of claim 3, wherein said forward edge ridge and said rearward edge ridge each have a diameter about 6 mm to about 22 mm.

5. The tampon applicator of claim 3, wherein said forward edge ridge and said rearward edge ridge are spaced apart about 13 mm to about 40 mm.

6. The tampon applicator of claim 3, wherein said finger grip section further comprises a finger accepting region formed between said forward edge ridge and said rearward edge ridge.

7. The tampon applicator of claim 6, wherein said finger accepting region has a diameter less than the diameter of said forward edge ridge and said rearward edge ridge.

8. The tampon applicator of claim 6, wherein said finger accepting region has a surface contour selected from the group consisting of concave, convex, flat, and any combinations thereof.

9. The tampon applicator of claim 6, wherein said finger accepting region has a maximum diameter to a minimum diameter ratio about 1.10 to about 1.75.

10. The tampon applicator of claim 9, wherein said ratio is about 1.25 to about 1.35.

11. The tampon applicator of claim 6, wherein said finger accepting region further comprises one or more gripping structures.

12. The tampon applicator of claim 11, wherein said one or more gripping structures are selected from the group consisting of embossments, protuberances, slits, grooves, louvers, perforations, lances, abrasive media, high wet coefficient of friction material, pressure sensitive adhesive, and any combinations thereof.

13. The tampon applicator of claim 11, wherein said one or more gripping structures are formed in a shape selected from the group consisting of arc, circle, concave, cone, convex, diamond, line, oval, polygon, rectangle, rib, square, triangle, and any combinations thereof.

14. The tampon applicator of claim 1, wherein said finger grip section further comprises a chamfer at a plunger receiving end.

15. The tampon applicator of claim 1, wherein said insertion tip section has a ratio of a maximum diameter of said insertion tip section to a total length of said insertion tip section about 0.9 to about 1.8.

16. The tampon applicator of claim 14, wherein said chamfer receives said plunger.

17. The tampon applicator of claim 1, wherein said barrel has a maximum diameter region formed where said main body section abuts said reverse taper section.

18. The tampon applicator of claim 17, wherein said maximum diameter is located on said barrel about 32 mm to about 54 mm from said insertion end of said barrel.

19. The tampon applicator of claim 1, wherein said plurality of petals is two or more petals.

20. The tampon applicator of claim 19, wherein said insertion tip section has about 3 to about 8 petals.

21. The tampon applicator of claim 19, wherein said ratio is about 1.1 to about 1.3.

22. The tampon applicator of claim 14, wherein said plunger has said flared end on said forward end, on said rearward end, or both on said forward end and said rearward end.

23. The tampon applicator of claim 1, wherein said plunger has a flared end on a forward end, on a rearward end, or both on said forward end and said rearward end.

24. The tampon applicator of claim 23, wherein said flared end on said forward end has a diameter about 6 mm to about 22 mm.

25. The tampon applicator of claim 23, wherein said flared end on said rearward end has a diameter about 5 mm to 20 mm.

26. The tampon applicator of claim 23, wherein said flared end on said rearward end has a fingertip accepting area.

27. The tampon applicator of claim 26, wherein said fingertip accepting area has a geometry selected from the group consisting of flat, concave, convex, and any combinations thereof.

28. The tampon applicator of claim 1, wherein said plunger has a diameter about 4 mm to about 18 mm.

29. The tampon applicator of claim 1, wherein said barrel, said plunger, or both said barrel and said plunger are formed from a material selected from the group consisting of biopolymer, cardboard, heat shrink plastic, paper slurry, plastic, plastic tubing, pulp slurry, pulp-molded paper, and any combinations thereof.

30. The tampon applicator of claim 1, wherein said barrel, said plunger, or both said barrel and said plunger, have a surface that is coated with a material selected from the group consisting of cellophane, cellulose, epoxy, lacquer, nitrocellulose, nylon, plastic, polyester, polylactide, polyolefin, polyvinyl alcohol, polyvinyl chloride, silicone, wax, and any combinations thereof.

31. The tampon applicator of claim 30, wherein said surface is an outside surface, an inner surface, and any combinations thereof.

32. The tampon applicator of claim 1, wherein said main body section has a maximum diameter section that is sensually perceivable to a user.

33. The tampon applicator of claim 1, wherein said main body section has a diameter along an entire length of said main body section and said reverse taper section has a diameter along an entire length of said reverse taper section that is greater than a diameter along an entire length of said finger grip section.

34. A tampon applicator comprising:
a barrel having a center axis, said barrel having a tubular shape between a first end and a second end, said first end having an insertion tip that is curved toward said first end, said insertion tip being connected to a main body section at a first plane, said main body section increasing in diameter from said first plane to a maximum diameter of said barrel, said main body section being connected to a reverse taper portion at said maximum diameter of said barrel, said reverse taper portion decreasing in diameter from said maximum diameter of said barrel toward a finger grip section, said reverse taper portion being connected to a forward edge of said finger grip section, said finger grip section decreasing in diameter from said forward edge in a finger accepting region, said finger accepting region increasing in diameter to said second end, said insertion tip section, said main body section, said reverse taper section and said finger grip section each entirely positioned about said center axis, and said portions of said center axis in said insertion tip section, said main body section, said reverse taper section and said finger grip section being entirely in the same plane; and a plunger telescopically received within said finger grip section, said plunger having a diameter slightly smaller than a smallest diameter of said finger grip section so that said plunger telescopically fits throughout an interior of said barrel, said plunger being unsupported by said main body section when positioned within said main body section.

35. The tampon applicator of claim 34, wherein said main body section increases in diameter from said first plane to said maximum diameter of said barrel and said reverse taper portion decreases in diameter from said maximum diameter of said barrel to said finger grip section to form a convex curve at said maximum diameter.

36. The tampon applicator of claim 35, wherein said main body section increases in diameter linearly or curvilinearly from said first plane to said maximum diameter of said barrel.

37. The tampon applicator of claim 34, wherein said barrel has an interior wall within said barrel and an exterior wall opposite said interior wall, and wherein said interior wall is sized along an entire length of said main body section and said reverse taper section to house a pledget.

* * * * *